United States Patent
Ji et al.

(10) Patent No.: US 10,820,826 B2
(45) Date of Patent: Nov. 3, 2020

(54) MULTIPLE OPTICAL FUSION-IMAGE BASED METHOD AND APPARATUS FOR DIAGNOSING BRAIN TUMOR IN REAL-TIME

(71) Applicant: INDUSTRY-ACADEMIC COOPERATION FOUNDATION, YONSEI UNIVERSITY, Seoul (KR)

(72) Inventors: Youngbin Ji, Goyang-si (KR); chulmin Joo, Goyang-si (KR); Seung Jae Oh, Gwangmyeong-si (KR); Jin Suck Suh, Seoul (KR); Yong Min Huh, Seoul (KR); Jong Hee Chang, Seoul (KR); Seok Gu Kang, Suwon-si (KR); Se Hoon Kim, Seoul (KR); Sang Hoon Kim, Seongnam-si (KR); Jung Heo, Seoul (KR)

( * ) Notice: Subject to any disclaimer, the term of this patent is extended or adjusted under 35 U.S.C. 154(b) by 344 days.

(21) Appl. No.: 15/759,451

(22) PCT Filed: Sep. 6, 2016

(86) PCT No.: PCT/KR2016/009972
§ 371 (c)(1),
(2) Date: Mar. 12, 2018

(87) PCT Pub. No.: WO2017/043839
PCT Pub. Date: Mar. 16, 2017

(65) Prior Publication Data
US 2018/0256065 A1    Sep. 13, 2018

(30) Foreign Application Priority Data
Sep. 11, 2015   (KR) .................. 10-2015-0128726

(51) Int. Cl.
| | | |
|---|---|---|
| *A61B 5/05* | (2006.01) | |
| *A61B 5/06* | (2006.01) | |
| *A61B 5/00* | (2006.01) | |

(52) U.S. Cl.
CPC .......... *A61B 5/0507* (2013.01); *A61B 5/0042* (2013.01); *A61B 5/0066* (2013.01);
(Continued)

(58) Field of Classification Search
CPC ... A61B 5/0507; A61B 5/0042; A61B 5/0066; A61B 5/0075
See application file for complete search history.

(56) References Cited

U.S. PATENT DOCUMENTS

| | | | |
|---|---|---|---|
| 2003/0100824 A1* | 5/2003 | Warren ................. | B05C 5/0216 600/407 |
| 2012/0120231 A1* | 5/2012 | Itani ...................... | G01S 7/4811 348/135 |

(Continued)

FOREIGN PATENT DOCUMENTS

| | | |
|---|---|---|
| JP | 2009-061034 | 3/2009 |
| JP | 2012-516206 | 7/2012 |

(Continued)

OTHER PUBLICATIONS

English Specification of 10-2000-0061358.
(Continued)

*Primary Examiner* — Rochelle D Turchen
(74) *Attorney, Agent, or Firm* — Antonio Ha & U.S. Patent, LLC (57) ABSTRACT

A method and an apparatus for diagnosing a brain tumor in real-time are disclosed. A method for detecting a brain tumor in real-time can comprise the steps of: generating, by a probe, a plurality of input signals and transferring the same to a target detection region which is estimated to be the
(Continued)

location of a brain tumor; receiving, by the probe, a plurality of reflection signals on the basis of a plurality of input signals; and detecting, by the probe, a plurality of the received reflection signals, wherein a plurality of the input signals comprise a terahertz signal, an optical coherence tomography (OCT) signal, and a Raman signal, and a plurality of the reflection signals can be used for generating a plurality of image information for detecting the location of a brain tumor; and an apparatus for diagnosing a brain tumor in vitro and in real-time, can be used to diagnose, in real-time, a brain tumor specimen, which is extracted from the brain.

2 Claims, 4 Drawing Sheets

(52) U.S. Cl.
CPC ............. *A61B 5/0075* (2013.01); *A61B 5/06* (2013.01); *A61B 5/4064* (2013.01); *A61B 5/72* (2013.01); *A61B 2576/026* (2013.01)

(56) References Cited

U.S. PATENT DOCUMENTS

| 2014/0358447 | A1* | 12/2014 | Doyle | ................. A61B 8/085 |
| | | | | 702/19 |
| 2016/0178439 | A1* | 6/2016 | Freudiger | ......... G01N 15/1434 |
| | | | | 356/301 |

FOREIGN PATENT DOCUMENTS

| JP | 2014-112078 | 6/2014 |
| KR | 10-2000-0061358 | 4/2002 |
| KR | 10-2009-0104224 | 10/2009 |
| KR | 10-2013-0056886 | 5/2013 |

OTHER PUBLICATIONS

English Specification of 10-2009-0104224.
English Abstract of 2014-112078.
English Abstract of 2009-061034.
English Specification of 10-2013-0056886.
English Abstract of 2012-516206.

* cited by examiner

MULTIPLE OPTICAL FUSION-IMAGE BASED METHOD AND APPARATUS FOR DIAGNOSING BRAIN TUMOR IN REAL-TIME

CROSS-REFERENCE TO RELATED APPLICATIONS

This patent application is a national-stage application of International Patent Application No. PCT/KR2016/009972, filed on Sep. 6, 2016, which claims priority under 35 U.S.C. § 119 to Korean Patent Application No. 10-2015-0128726, filed on Sep. 11, 2015, in the Korean Intellectual Property Office, the disclosure of which is incorporated by reference herein in its entirety.

TECHNICAL FIELD

The present invention relates to brain tumor diagnosing methods and apparatuses, and more specifically, to methods and apparatuses for real-time detecting/diagnosing brain tumors and performing brain tumor surgery based on multiple optical fusion images.

DISCUSSION OF RELATED ART

As per international census statistics, about 10 out of a population of 100,000 are newly diagnosed of brain tumor every year, and domestically, 2,500 to 4,500 new cases are reported. Currently, patients with a brain tumor are estimated to reach nearly 20,000. Primary brain tumors which occur in intracranial tissues come in various types; among them, those malignant are known to have a bad prognosis, and in particular, glioblastoma, a type of glioma, has a worse prognosis with the median length of survival of 14.6 months despite aggressive treatment.

For malignant brain tumors, the best treatment thus far known to have a good prognosis is a surgical total resection of the tumor. Benign brain tumors should also be fully removed because they can develop to malignant ones if they grow in the limited cranial cavity. A primary method currently used to diagnose brain tumors before surgery is magnetic resonance imaging (MRI). However, traditional MRI techniques cannot be put to use during surgery. Furthermore, brain tumors are not recognized well by human eyes, posing a difficulty in fully removing them. The human brain is tied with a diversity of nervous systems, such as of cognition, vision, and tactile sensation. Thus, normal brain tissues should remain reserved as intact as possible while removing brain tumor tissues. This puts more importance on technology to identify the border of the brain tumor tissue during surgery.

Current major approaches to detecting the border of brain tumor during surgery are to use surgical microscopy or neuro-navigation. However, these ways do not fully work due to so-called 'brain shift' that occurs during the surgery by utilizing MRI images pre-captured.

To overcome these problems, intraoperative MRI (iMRI) devices have been developed and used which are available for surgery; however, their issues with high cost and an extra delay in surgical time puts a plenty of limitations on their actual use in clinics.

A state-of-the-art technology among those to detect the border of brain tumor during surgery is fluorescent imaging adopting a special contrast medium called aminolaevulinic acid (ALA). This technique exhibits a superior capability of border detection for glioblastoma, which is WHO grade III or IV malignant, but not for WHO grade II brain tumors.

Meanwhile, terahertz (THz) waves are electromagnetic waves whose frequency band ranges from 50 GHz to 10 THz, gradually attracting more and more attention worldwide as future radio wave resource with the recent development of technology, and it becomes more critical in various applications as converging with information technology (IT) and bio-technology (BT).

PRIOR TECHNICAL DOCUMENTS

Patent Documents (Patent Document 1) KR 10-2000-0061358

SUMMARY

An aspect of the present invention provides a method for diagnosing a brain tumor in real-time.

Another aspect of the present invention provides an apparatus for diagnosing a brain tumor in real-time.

Still another aspect of the present invention provides an apparatus for removing a brain tumor in real-time.

According to an aspect of the present invention, a method for detecting a brain tumor in real-time may comprise producing a plurality of input signals and transferring the input signals to a target detection area where the brain tumor is estimated to be positioned, by a probe, receiving a plurality of reflected signals based on the plurality of input signals, by the probe, and detecting the plurality of reflected signals received, by the probe, the plurality of input signals may include a terahertz signal, an optical coherence tomography (OCT) signal, and a Raman signal, and the plurality of reflected signals may be used to produce information about a plurality of images to detect the position of the brain tumor.

Meanwhile, the plurality of input signals may further include a fluorescent signal, and the terahertz signal is an electromagnetic wave in the form of a continuous wave or pulse wave having a frequency band ranging from 0.05 THz to 30 THz, the OCT signal may be a signal with a wavelength ranging 600 nm to 1400 nm produced by a broadband wavelength light source for optical coherence tomography, the Raman signal may be a signal with a wavelength ranging from 200 nm to 1400 nm produced by a broadband wavelength light source for Raman spectroscopy and imaging, and the fluorescent signal may be a signal produced based on a contrast medium.

The plurality of reflected signals may be total-reflected or transmitted by an indium tin oxide (ITO) glass, and among the plurality of reflected signals, the terahertz signal may be total-reflected by the ITO glass, and the OCT signal, the Raman signal, and the fluorescent signal may be transmitted through the ITO glass.

The plurality of images may include a first image, a second image, and a third image, and the first image may be a image produced based on the terahertz signal, the second image may be an image produced based on the OCT signal, the Raman signal, and the fluorescent signal, and the third image may be a fusion image of the first image and the second image.

The method may further comprise producing a plurality of second input signals and transferring the second input signals to a brain tumor sample, by an in-vitro real-time brain tumor diagnosing apparatus, receiving a plurality of second reflected signals based on the plurality of second input signals, by the in-vitro real-time brain tumor diagnosing apparatus, and producing information about a plurality of images for the brain tumor sample based on the plurality of second reflected signals, by the in-vitro real-time brain tumor diagnosing apparatus, the plurality of second input signals may include a second terahertz signal, a second OCT signal, and a second Raman signal, and each of the plurality of second input signals may share the same signal source as a respective one of the plurality of input signals.

According to another aspect of the present invention, an apparatus for detecting a brain tumor in real-time may comprise a signal producer implemented for a probe to produce a plurality of input signals and transfer the input signals to a target detection area where the brain tumor is estimated to be positioned and a signal detector implemented for the probe to receive a plurality of reflected signals based on the plurality of input signals and to detect the plurality of reflected signals received, the plurality of input signals may include a terahertz signal, an optical coherence tomography (OCT) signal, and a Raman signal, and the plurality of reflected signals may be used to produce information about a plurality of images to detect the position of the brain tumor.

Meanwhile, the plurality of input signals may further include a fluorescent signal, and the terahertz signal may be an electromagnetic wave in the form of a continuous wave or pulse wave having a frequency band ranging from 0.05 THz to 30 THz, the OCT signal may be a signal with a wavelength ranging 600 nm to 1400 nm produced by a broadband wavelength light source for optical coherence tomography, the Raman signal may be a signal with a wavelength ranging from 200 nm to 1400 nm produced by a broadband wavelength light source for Raman spectroscopy and imaging, and the fluorescent signal may be a signal produced based on a contrast medium.

The plurality of reflected signals are total-reflected or transmitted by an indium tin oxide (ITO) glass, and among the plurality of reflected signals, the terahertz signal may be total-reflected by the ITO glass, and the OCT signal, the Raman signal, and the fluorescent signal are transmitted through the ITO glass.

The plurality of images may include a first image, a second image, and a third image, and the first image may be a image produced based on the terahertz signal, the second image may be an image produced based on the OCT signal, the Raman signal, and the fluorescent signal, and the third image may be a fusion image of the first image and the second image.

The apparatus may further comprise a second producer implemented for an in-vitro real-time brain tumor diagnosing apparatus to produce a plurality of second input signals and transfer the second input signals to a brain tumor sample, a second signal detector implemented for the in-vitro real-time brain tumor diagnosing apparatus to detect a plurality of second reflected signals based on the plurality of second input signals, and an image producer implemented to produce information about a plurality of images for the brain tumor sample based on the plurality of second reflected signals, the plurality of second input signals may include a second terahertz signal, a second OCT signal, and a second Raman signal, and each of the plurality of second input signals shares the same signal source as a respective one of the plurality of input signals.

According to still another aspect of the present invention, a brain tumor surgical apparatus may comprise an image receiving and analyzing unit implemented to receive a plurality of images related to a brain tumor and analyze a position of the brain tumor, a first positioner implemented to determine a first position that is an initial position for removing the brain tumor by a brain tumor remover included in the brain tumor surgical apparatus, a second positioner implemented to determine a second position varied to remove the brain tumor by the brain tumor remover according to a variation in position of a patient's brain, the brain tumor remover, or the brain tumor surgical apparatus, a brain tumor cutting surface determiner implemented to determine a brain tumor cutting surface based on the first position and the second position, and the brain tumor remover implemented to remove the brain tumor according to the brain tumor cutting surface.

Meanwhile, the brain tumor cutting surface may be determined so that the area of a surface to be cut to remove the brain tumor is minimized based on the position of the brain tumor.

The plurality of images are obtained based on a probe, the probe may be implemented to produce a plurality of input signals and transfer the input signals to a target detection area where the brain tumor is estimated to be positioned, to receive a plurality of reflected signals based on the plurality of input signals, and to detect the plurality of reflected signals received, the plurality of input signals may include a terahertz signal, an OCT signal, and a Raman signal, and the plurality of reflected signals are used to produce the plurality of images.

The plurality of input signals may further include a fluorescent signal, and the terahertz signal may be an electromagnetic wave in the form of a continuous wave or pulse wave having a frequency band ranging from 0.05 THz to 30 THz, the OCT signal may be a signal with a wavelength ranging 600 nm to 1400 nm produced by a broadband wavelength light source for optical coherence tomography, the Raman signal may be a signal with a wavelength ranging from 200 nm to 1400 nm produced by a broadband wavelength light source for Raman spectroscopy and imaging, and the fluorescent signal may be a signal produced based on a contrast medium.

The plurality of images may include a first image, a second image, and a third image, and the first image may be a image produced based on the terahertz signal, the second image may be an image produced based on the OCT signal, the Raman signal, and the fluorescent signal, and the third image may be a fusion image of the first image and the second image.

Embodiments of the present invention enables detection of the border of brain tumor by use of a small portable probe that can be carried in one hand, free from an extra time delay in surgery, and eliminating the need for moving the patient or massive equipment.

Further, it is possible to detect low-grade brain tumors which are difficult to detect according to the prior art, as well as existing high-grade malignant brain tumors. Also possible are detection and diagnosis of brain tumor tissues within a very short time (one minute or less) with high sensitivity and specificity. Combining with conventional fluorescent technology using a contrast medium may deliver more accurate diagnosis and detection of high-grade brain tumor tissues.

DETAILED DESCRIPTION OF EXEMPLARY EMBODIMENTS

Particular embodiments of the present invention are described below with reference to the accompanying drawings. The embodiments are described thoroughly enough for one of ordinary skill in the art to practice the present invention.

It should be appreciated that various embodiments of the present invention, although differing from each other, are not necessarily exclusive of each other. For example, the particular shapes, structures, and features related to one embodiment as set forth herein may also be implemented in other embodiments without departing from the spirit and scope of the present invention.

It also be noted that changes may be made to the positions or arrangement of individual components in embodiments disclosed without departing from the spirit and scope of the present invention. Thus, the following detailed description is not intended as limiting, and the scope of the present invention is defined solely by the appended claimed along with all equivalents of the claims. Similar reference denotations refer to the same or similar features in various aspects throughout the drawings.

Hereinafter, preferred embodiments of the present invention are described in detail with reference to the accompanying drawings.

Among others, terahertz (THz) waves, by their nature of traveling straight as does visible light and being transmitted well through various materials, are in wide use for, e.g., detecting forged notes, explosives, or biochemical weapons, but not only in basic science sectors, such as physics, chemistry, biology, or medical science. In particular, terahertz waves are able to sensitively measure the content of water and fat, coming into vigorous use in biomedical applications.

Optical coherence tomography is an image technology to deliver high resolution and structural information, and this technique is capable of tomographic information about a biometric tissue which is about 2 mm to 3 mm deep, putting to vigorous use in biomedical industry; especially, this technique is already in commercial use in the field of eye exams.

Raman spectroscopy and imaging is a technique that detects a scattering disparity of incident light by, e.g., unique frequency of biometric tissue, enabling characteristic distinction of the molecular structure of deoxyribonucleic acid (DNA) of fat or protein, recently subjected to wide use in biomedical applications.

According to the present invention, a real-time brain tumor border detection and depiction method is disclosed which takes advantage of THz waves, optical coherence tomography, Raman spectroscopy and imaging, and fluorescent technology.

According to an embodiment of the present invention, use of the real-time brain tumor diagnosis enables real-time detection and depiction of the border of malignant glioma or other brain tumors during surgery by combining THz wave, optical coherence tomography, Raman spectroscopy and imaging, and fluorescent techniques.

Further, according to an embodiment of the present invention, the use of the real-time brain tumor diagnosis enables diagnosis of a brain tumor in real-time without a high-cost contrast medium, freeing side effects due to a contrast medium and allowing for low-cost detection of a brain tumor during surgery.

Further, according to an embodiment of the present invention, the use of the real-time brain tumor diagnosis ensures detection of low-grade brain tumors which are conventionally difficult to detect, as well as high-grade, malignant brain tumors.

Still further, according to an embodiment of the present invention, the use of the real-time brain tumor diagnosis is free from an extra time delay in surgery, eliminates the need for moving the patient or massive equipment, and allows detection of the border of brain tumor by use of a small portable probe that can be carried in one hand.

Also possible by using the real-time brain tumor diagnosis, according to an embodiment of the present invention, are detection and diagnosis of a brain tumor tissue within a pretty short time (e.g., one minute or less) with high sensitivity and specificity.

Further, the real-time brain tumor diagnosis used according to an embodiment of the present invention combines with a fluorescent technique using a contrast medium, enabling detection and diagnosis of high-grade brain tumor tissues at higher accuracy.

According to an embodiment of the present invention, in the real-time brain tumor diagnosis, a terahertz technique capable of quick diagnosis of a broader area despite its relatively low resolution may first be applied, followed by a Raman technique being applied onto the border portion of the brain tumor in the terahertz image, so as to achieve increased accuracy and reduced surgery time.

Now described are a specific real-time brain tumor diagnosis method and apparatus.

Figure 1:
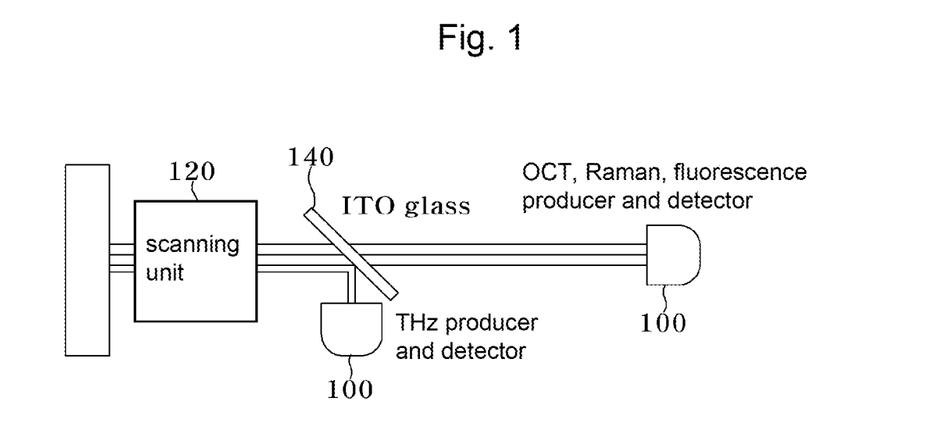
FIG. 1 is a concept view illustrating a probe for real-time diagnosis of a brain tumor according to an embodiment of the present invention.

FIG. 1 is a concept view illustrating a probe for diagnosing a brain tumor in real-time according to an embodiment of the present invention.

FIG. 1 illustrates a probe included in a real-time brain tumor diagnosing apparatus according to an embodiment of the present invention.

Referring to FIG. 1, the probe may include a signal producing and detecting unit 100 that produces a wavelength for detecting a brain tumor, a scanning unit 120, and an indium tin oxide (ITO) glass 140.

The signal producing and detecting unit 100 may include a terahertz wave producer/terahertz wave detector that produces and detects terahertz signals, an optical coherence tomography (OCT) producer/OCT detector that produces and detects OCT signals for optical coherence tomography, a Raman producer/Raman detector that produces and detects Raman signals for Raman spectroscopy and imaging, and a fluorescence producer/fluorescence detector that produces fluorescent signals based on a contrast medium. The signal producing and detecting unit 100 may also be represented as a signal producer or signal detector.

The scanning unit (or a scanner) 120 may be implemented to perform scanning to produce images. For example, the scanning unit 120 may be an optical device, such as a galvanometer, used to combine signals into an image based on a raster scan. The scanning unit 120 may perform scanning to produce a two-dimensional (2D) image and/or a three-dimensional (3D) image based on various focused signals (a terahertz signal, an OCT signal, a Raman signal, and a fluorescent signal) to produce an image. Upon using an array-concept detector of a charge-coupled device (CCD) camera type, such as a photographing type, rather than a raster scan type, the scanning unit 120 may be excluded from the probe.

The ITO glass 140 may be implemented to total-reflect the terahertz signal while transmitting signals of the wavelengths corresponding to the Raman signal, OCT signal, and fluorescent signal, thereby determining the paths of the terahertz signal, the Raman signal, the OCT signal, and the fluorescent signal.

The specific operation of each module included in the signal producing and detecting unit 100 is as follows.

The terahertz wave producer/terahertz wave detector may be implemented to produce and detect terahertz signals. Terahertz signals produced and detected by the terahertz wave producer/terahertz wave detector may be electromagnetic waves whose frequency band ranges from 0.05 THz to 30 THz. Further, terahertz signals may be terahertz waves in the form of pulse waves or continuous waves. The terahertz wave producer/terahertz wave detector may include an optical fiber.

The OCT producer/OCT detector may be implemented to produce and detect OCT signals. OCT signals may be signals produced from a broadband wave light source that produces signals ranging from 600 nm to 1400 nm. For example, the broadband wave light source may be a swept-source laser, a super-luminescent laser diode, or a super-continuum. The OCT detector may be implemented to allow an optical signal returning from a sample arm and an optical signal coming back from a reference arm to interfere with each other via use of interferometry to detect the interference signal. The OCT detector may include an optical fiber.

The Raman producer/Raman detector may be implemented to produce and detect Raman signals. Raman signals may be signals produced from a broadband wave light source that produces signals ranging from 200 nm to 1400 nm. For example, the wideband wave light source may be a swept-source laser, a super-luminescent laser diode, or a super-continuum laser. The Raman detector may include a Raman scattering spectroscope, CCD camera, or optical detector capable of measuring Raman signals scattered from incident light.

The fluorescence producer/fluorescence detector may be implemented based on all light sources including a fluorescent emission wavelength of a contrast medium, such as a laser, a laser diode, or a light-emitting diode (LED). The fluorescence detector capable of detecting a fluorescent emission produced by the contrast medium may include a CCD camera or an optical detector. Further, the fluorescence detector may include an optical filter or a beam splitter to separate the wavelength of the fluorescent emission from the other wavelengths so as to detect only the wavelength of the fluorescent emission.

The probe may further include a processor which may be implemented to control the operations of the signal producing and detecting unit and the scanning unit.

The probe may add a location information-related component to determine and gather information about the probe's current location in 3D.

According to an embodiment of the present invention, the real-time brain tumor diagnosing apparatus may include an additional image producing and detecting device that shares a light source with the probe.

Figure 2:
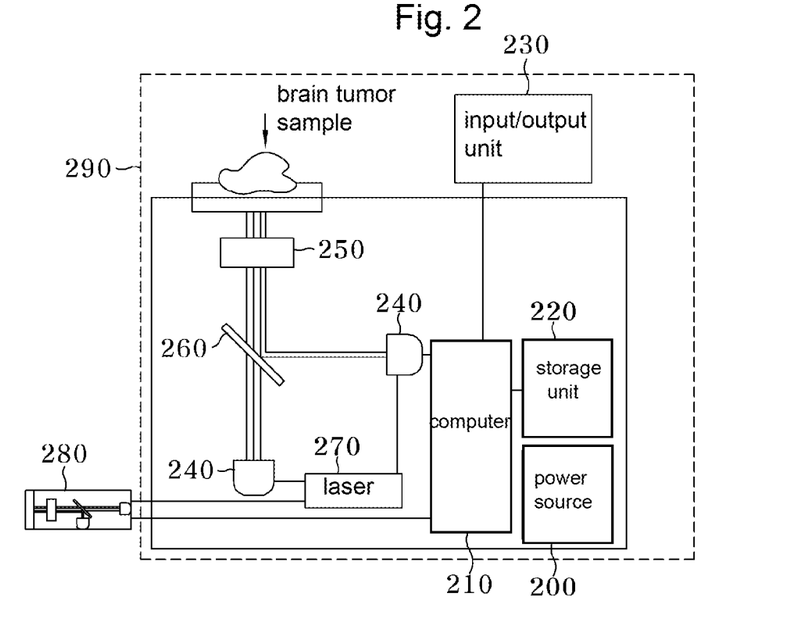
FIG. 2 is a concept view illustrating a real-time brain tumor diagnosing apparatus including a probe according to an embodiment of the present invention.

FIG. 2 is a concept view illustrating a real-time brain tumor diagnosing apparatus including a probe according to an embodiment of the present invention.

Referring to FIG. 2, the brain tumor diagnosing apparatus may an in-vitro real-time brain tumor detector 290 that shares a light source (or a laser) 270 with a probe 280. The probe 280 may be represented as a first real-time brain tumor diagnosing apparatus, and the in-vitro real-time brain tumor detector 290 may be represented as a second real-time brain tumor diagnosing apparatus.

The in-vitro real-time brain tumor diagnosing apparatus (or second real-time brain tumor diagnosing apparatus) 290 may include a power source 200, a processor (or computer) 210, a storage unit 220, an input/output unit 230, a second signal producing and detecting unit 240, a second scanning unit 250, and a second ITO glass 260.

The power source 200 may be implemented to feed power to each component of the probe (first real-time brain tumor diagnosing apparatus) 280 and/or each component of the in-vitro real-time brain tumor diagnosing apparatus (for example, the second real-time brain tumor diagnosing apparatus) 290.

The processor 210 may be implemented to control the operation of the components of each of the first real-time brain tumor diagnosing apparatus 280 and/or the second real-time brain tumor diagnosing apparatus 290.

The storage unit 220 may be implemented to store signals and image data produced by the first real-time brain tumor diagnosing apparatus 280 and/or the second real-time brain tumor diagnosing apparatus 290. The storage unit 220 may be implemented to further store information about the location where image data is obtained by the probe 280.

The input/output unit 230 may include, e.g., an interface (e.g., a mouse, a keyboard, or a touchscreen) enabling input of commands to the first real-time brain tumor diagnosing apparatus 280 and/or the second real-time brain tumor diagnosing apparatus 290 and a monitor for outputting image information and results of computation.

The second signal producing and detecting unit 240 may include a second terahertz wave producer/second terahertz wave detector that produces and detects second terahertz signals, a second OCT producer/second OCT detector that produces and detects second OCT signals for optical coherence tomography, a second Raman producer/second Raman detector that produces and detects second Raman signals for Raman spectroscopy and imaging, and a second fluorescence producer/second fluorescence detector that emits second fluorescent signals based on a contrast medium.

The second scanning unit 250 may be implemented to perform scanning to produce images. The scanning unit 250 may perform scanning to produce images based on various focused signals (e.g., the second terahertz signal, second OCT signal, second Raman signal, and second fluorescent signal) to produce images. Upon using a detector of an array concept which is of a photographing type, e.g., CCD camera, rather than the raster scan type, the second scanning unit 250 may be excluded from the in-vitro real-time brain tumor diagnosing apparatus.

The second ITO glass 260 may total-reflect the second terahertz signal while transmitting signals of wavelengths corresponding to the second Raman signal, second OCT signal, and second fluorescent signal, thereby determining the paths of the second terahertz signal, second Raman signal, second OCT signal, and second fluorescent signal.

According to an embodiment of the present invention, the first signal producing and detecting unit of the first real-time brain tumor diagnosing apparatus (e.g., the probe) 280 and the second signal producing and detecting unit of the second real-time brain tumor diagnosing apparatus (e.g., the in-vitro real-time brain tumor diagnosing apparatus) 290 may share the light source (or a laser or a signal source) 270. That is, a signal (or laser) 270 for producing the terahertz signal, OCT signal, Raman signal, and fluorescent signal may be shared between the first signal producing and detecting unit and the second signal producing and detecting unit.

Further, according to an embodiment of the present invention, the ITO glass 260 may be formed of a material, e.g., a conductive transparent board, to reflect the terahertz signal while transmitting the OCT signal, Raman signal, and fluorescent signal except for the terahertz signal to allow the terahertz signal, OCT signal, Raman signal, and fluorescent signal to have the same path. The scanning unit 250 may be implemented to simultaneously scan the terahertz signal, OCT signal, Raman signal, and fluorescent signal on the same path.

Further, according to an embodiment of the present invention, the ITO glass 260 may be formed of a material, e.g., polymer, to transmit the terahertz signal while reflecting the OCT signal, Raman signal and fluorescent signal except for the terahertz signal, allowing the terahertz signal, OCT signal, Raman signal, and fluorescent signal to have the same path. The scanning unit 250 may be implemented to simultaneously scan the terahertz signal, OCT signal, Raman signal, and fluorescent signal on the same path.

Further, according to an embodiment of the present invention, the ITO glass 260 may be implemented to allow the terahertz signal and the other signals, i.e., the OCT signal, Raman signal, and fluorescent signal to have inconsistent paths. The scanning unit 250 may be implemented to simultaneously scan the terahertz signal, OCT signal, Raman signal, and fluorescent signal on the inconsistent paths.

Further, according to an embodiment of the present invention, the signal source of the terahertz wave producer that produces the terahertz signal and the signal source of the OCT producer that produces the OCT signal may be the same light source.

Further, according to an embodiment of the present invention, it can be possible to perform diagnosis by measuring signals and images of low-grade and high-grade brain tumor tissue based on the other terahertz signal, OCT signal, and Raman signal than the fluorescent signal without using a contrast medium for obtaining the terahertz signal. As necessary, a contrast medium to obtain the fluorescent signal may be together used to raise the accuracy of detection and diagnosis of the brain tumor tissue.

Further, according to an embodiment of the present invention, it may be possible to diagnose and analyze various biometric tissues, as well as brain tumors, based on the terahertz signal, OCT signal, Raman signal, and fluorescent signal. Specifically, the real-time brain tumor diagnosing method according to an embodiment of the present invention may be used to detect images and signals and diagnose central nervous system tumor tissues (e.g., spinal cancer), as well as brain tumors.

Figure 3:
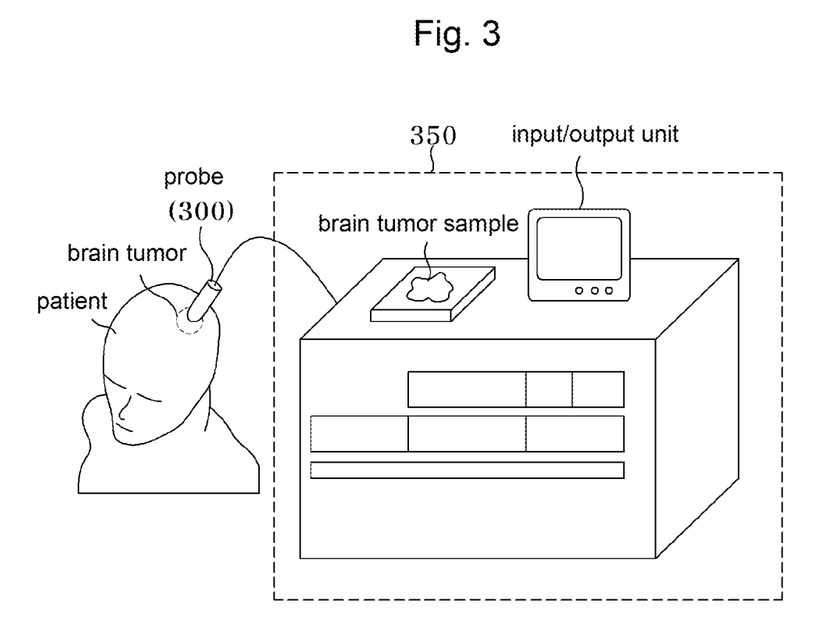
FIG. 3 is a concept view illustrating a real-time brain tumor diagnosing apparatus according to an embodiment of the present invention.

FIG. 3 is a concept view illustrating a real-time brain tumor diagnosing apparatus according to an embodiment of the present invention.

FIG. 3 is a concept view illustrating a brain tumor diagnosing method utilizing the real-time brain tumor diagnosing apparatus described above in connection with FIG. 2.

Referring to FIG. 3, the real-time brain tumor diagnosing apparatus may perform scanning on a brain tumor, with the probe 300 in direct contact with the patient's head. A first terahertz signal, a first OCT signal, a first Raman signal, and a first fluorescent signal may be output through signal input/output terminals of the probe 300 and may reach the patient's head and be reflected and input back to the probe 300.

The in-vitro real-time brain tumor diagnosing apparatus 350 may be used for separate diagnosis on a brain tumor sample. The brain tumor sample may be placed on a brain tumor sample loader that is positioned on the top of the in-vitro real-time brain tumor diagnosing apparatus 350. A second terahertz signal, a second OCT signal, a second Raman signal, and a second fluorescent signal may be output through signal input/output terminals of the in-vitro real-time brain tumor diagnosing apparatus 350, reach the brain tumor sample, and be reflected and input back to the in-vitro real-time brain tumor diagnosing apparatus 350.

Figure 4:
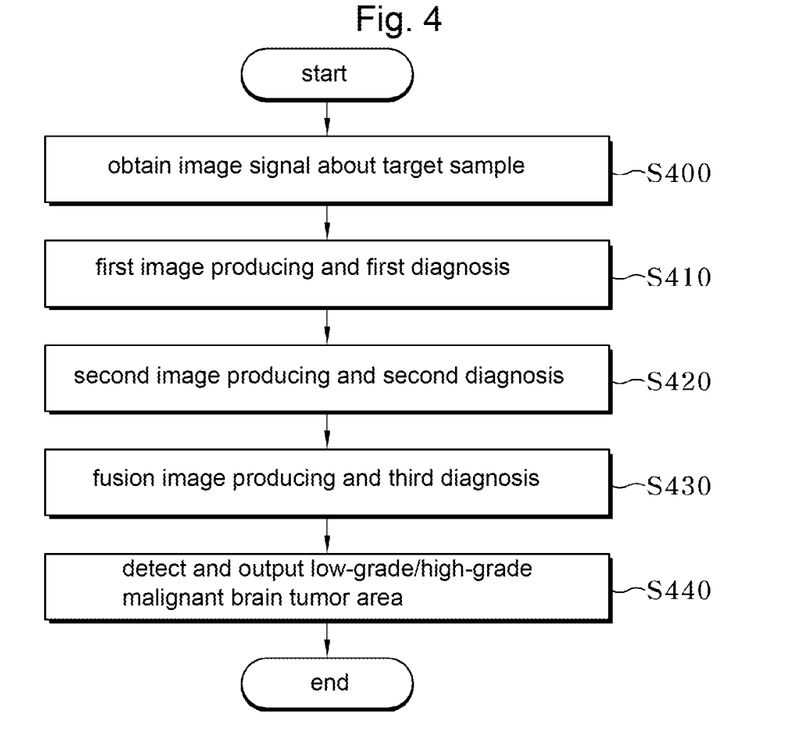
FIG. 4 is a flowchart illustrating a method for diagnosing a brain tumor according to an embodiment of the present invention.

FIG. 4 is a flowchart illustrating a method for diagnosing a brain tumor according to an embodiment of the present invention.

The brain tumor diagnosing method shown in FIG. 4 may sequentially be carried out based on a plurality of analysis steps. The term "sample" as used hereafter may mean a target sample inside the patient's head or a target sample extracted from the patient's body which is analyzed based on the probe or the in-vitro real-time brain tumor diagnosing apparatus.

Referring to FIG. 4, the real-time brain tumor diagnosing apparatus obtains an image signal for the target sample based on a terahertz signal, an OCT signal, and a Raman signal, and a fluorescent signal (optional) (step S400).

As set forth above, the terahertz signal, OCT signal and Raman signal, and fluorescent signal (optional) may be output and input through the probe and/or the in-vitro real-time brain tumor diagnosing apparatus, producing an image signal to create an image.

The real-time brain tumor diagnosing apparatus produces a first image, performing first diagnosis on the target sample (step S410).

The first image may be an image produced based on the terahertz signal. In other words, the first image is generated based on the terahertz signal except for the OCT signal and Raman signal and fluorescent signal (optional), and the first diagnosis may be carried out on the target sample based on the first image.

The real-time brain tumor diagnosing apparatus produces a second image, performing second diagnosis on the target sample (step S420).

The second image may be generated based on the OCT signal and Raman signal and fluorescent signal (optional) except for the terahertz signal. The second diagnosis may be performed on the target sample based on the second image.

The real-time brain tumor diagnosing apparatus fuses the first image and the second image to generate a fusion image and performs third diagnosis (step S430).

A third image may be generated by fusing the first image and the second image, and cross-validation may be carried out. Featuring points of the brain tumor in the first image and the second image may be analyzed to fuse the first image and the second image. The featuring points may be points that may show features in the image, e.g., where multiple edges meet, by image analysis. The third image may be produced based on the matching between the featuring points of the first image and the featuring points of the second image.

A low-grade/high-grade malignant brain tumor area is detected and output (step S440).

The low-grade/high-grade malignant brain tumor area may be detected from the target sample based on the first, second, and third images and may be output through an output unit.

Figure 5:
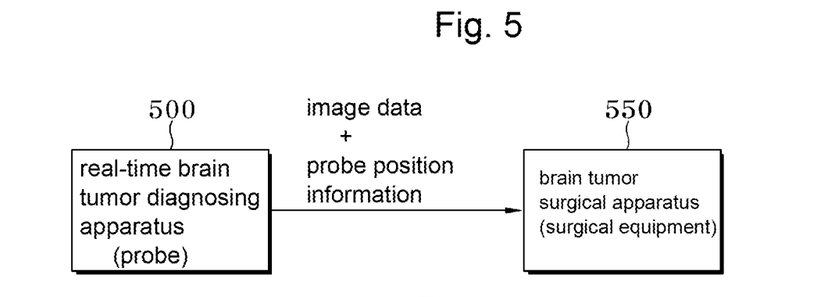
FIG. 5 is a concept view illustrating a method for removing a brain tumor in real-time according to an embodiment of the present invention.

FIG. 5 is a concept view illustrating a method for removing a brain tumor in real-time according to an embodiment of the present invention.

FIG. 5 discloses a procedure for removing a brain tumor in real-time by a surgical apparatus based on images obtained by the real-time brain tumor diagnosing apparatus.

Referring to FIG. 5, the position of a brain tumor may be analyzed through each of a plurality of images obtained by the real-time brain tumor diagnosing apparatus 500 based on a plurality of signals.

The position of the brain tumor may be analyzed with respect to the position which the surgical apparatus 550 for removing the brain tumor approaches. For example, a person's head may be analyzed for its shape, and the surgical apparatus may be inserted onto a particular area of her head to remove the brain tumor. The particular area where the surgical apparatus 550 is inserted may be termed a "brain tumor removal target area."

The probe 500 may obtain a plurality of images by scanning on the brain tumor removal target area. The image information obtained by the probe 500 may include a position, in 3D, of the probe 500 corresponding to a particular point of the brain tumor removal target area and image data corresponding to the 3D position of the probe 500. For example, the image information may include, as metadata, the 3D position of the probe 500 where the image information has been obtained.

The image information including the 3D position information about the probe 500 may be input to the surgical apparatus (brain tumor surgical apparatus) 550. Where the brain tumor is removed by the surgical apparatus 550, the 3D position information about the surgical apparatus 550 may correspond to the 3D position information about the probe 500. Depending on the position of approach of the surgical apparatus 550, the 3D position of the surgical apparatus 550 may be varied, and according to the varying 3D position of the surgical apparatus 550, the 3D position information about the probe 500 may be rendered to correspond thereto, and the image information as per the 3D position of the surgical apparatus 550 may be provided to the surgical apparatus 550.

The surgical apparatus 550 may determine the position of the brain tumor with respect to the position of the surgical apparatus 550 based on the image information received, and surgery for removing the brain tumor may be performed using a brain tumor remover according to the determined position of the brain tumor. The use of such method allows the surgical apparatus 550 to correspond in position to the probe 500 in real-time, enabling removal of the brain tumor portion in an accurate fashion.

Figure 6:
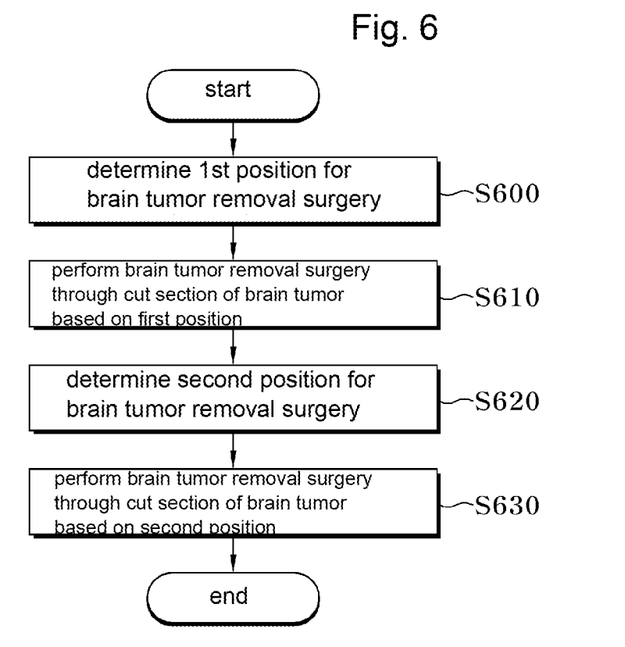
FIG. 6 is a flowchart illustrating a procedure for removing a brain tumor portion according to an embodiment of the present invention.

FIG. 6 is a flowchart illustrating a procedure for removing a brain tumor portion according to an embodiment of the present invention.

FIG. 6 discloses a specific resection procedure of a brain tumor portion using a surgical apparatus for brain tumor resection. FIG. 6 sets forth a method for performing surgery for removing a brain tumor by determining the start position of the surgical apparatus in the surgery and additionally obtaining adaptively image information about the brain tumor according to variations in position of the surgical apparatus.

Referring to FIG. 6, the surgical apparatus determines a first position where the brain tumor removal surgery will start of the removal target area based on the image information received from the real-time brain tumor diagnosing apparatus (step S600).

Specifically, the surgical apparatus may commence the brain tumor removal procedure in the first position. The first position may be where removal of the brain tumor is easiest or causes the least damage as determined based on the image information by the surgical apparatus. The first position may be determined based on various methods. For example, the surgical apparatus may determine, as the first position, a position where removing the brain tumor would likely result in the least side effects upon inserting the surgical apparatus based on the image information. Specifically, the position of a portion which would be least damaged but not fatal when removed from the brain may be determined as the first position.

After the first position is determined, the surgical apparatus proceeds with the brain tumor removal surgery based on a first brain tumor cutting surface determined with respect to the first position (step S610).

The brain tumor removal procedure may go on the first brain tumor cutting surface determined based on the position of the brain tumor and the first position. The brain tumor cutting surface may be a surface that surrounds the brain tumor to prevent the brain tumor from spreading. The brain tumor cutting surface may be determined based on various methods. The brain tumor cutting surface may be polygonal in shape to minimize the cutting surface given the 3D position of the brain tumor which has been simulated based on the image information.

A second position where the brain tumor removal surgery is performed is determined based on the image information corresponding to variations in position of the surgical apparatus (step S620).

The surgical apparatus (or a brain tumor remover included in the surgical apparatus) may be repositioned according to the procedure of cutting the brain tumor. For example, the surgical apparatus may be moved by an external force or the brain shift during surgery, or for cutting on the first brain tumor cutting surface. Where the surgical apparatus is relocated, the second position is determined as per the variation in position of the surgical apparatus, and a brain tumor cutting surface may be determined or a cutting procedure may be performed on the brain tumor cutting surface already determined, based on image information corresponding to the position varied.

After the second position is determined, the surgical apparatus performs the brain tumor removal surgery based on the brain tumor cutting surface determined with respect to the second position (step S630).

The brain tumor removal procedure on the second brain tumor cutting surface determined based on the position of the brain tumor and the second position may be performed, or an additional cutting procedure on the existing first brain tumor cutting surface may be performed based on the second position. The second brain tumor cutting surface may be determined so that the remaining cutting surface except for the cutting surface where the cutting has thus far been performed is minimized. Specifically, where the surgical apparatus is moved simply by an external force or due to a brain shift during surgery, the second brain tumor cutting surface may be redetermined. Whether the surgical apparatus is moved to cut on the first brain tumor cutting surface, an additional cutting procedure may be carried out on the existing first brain tumor cutting surface.

Figure 7:
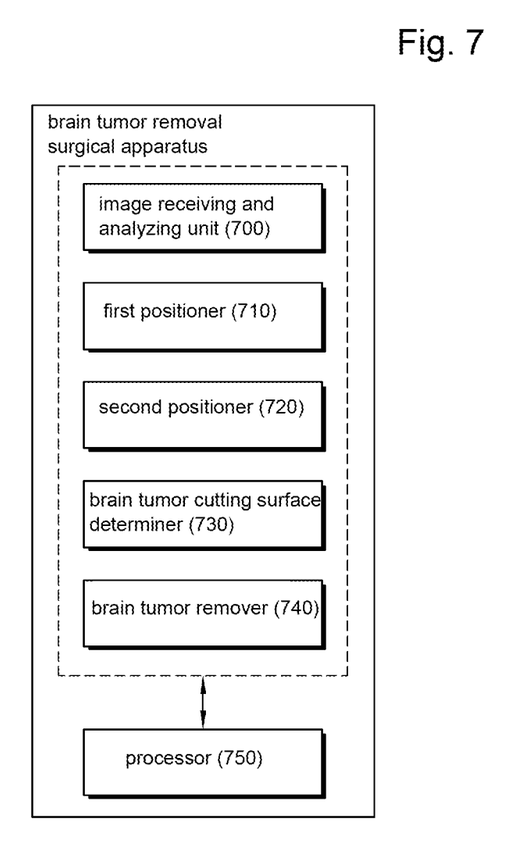
FIG. 7 is a concept view illustrating a surgical device for removing a brain tumor according to an embodiment of the present invention.

FIG. 7 is a concept view illustrating a brain tumor removal surgical apparatus according to an embodiment of the present invention.

Referring to FIG. 7, the brain tumor removal surgical apparatus may include an image receiving and analyzing unit 700, a first positioner 710, a second positioner 720, a brain tumor cutting surface determiner 730, a brain tumor remover 740, and a processor 750.

The image receiving and analyzing unit 700 may be implemented to receive an image signal from a real-time brain tumor diagnosing apparatus and to analyze the received image signal.

The first positioner 710 may be implemented to determine a first position where brain tumor removal surgery is to be performed. The first positioner 710 may analyze the position of each portion of the patient's brain based on image information and determine the first position for the brain tumor remover to approach the brain tumor for a brain tumor removal procedure.

The second positioner 720 may be implemented to determine a second position where brain tumor removal surgery is to be performed. Where the surgical apparatus is repositioned, the brain is shifted, or the brain tumor remover changes its path to remove the brain tumor, the second positioner 720 may analyze the position of each portion of the patient's brain and determine the second position for the brain tumor remover to approach the brain tumor for the brain tumor removal procedure.

The brain tumor cutting surface determiner 730 may be implemented to determine a brain tumor cutting surface where a removal procedure is to be performed by the brain tumor remover to remove the brain tumor. The brain tumor cutting surface determiner 730 may determine a polygonal brain tumor cutting surface that surrounds the brain tumor with respect to the first position and/or the second position. The polygonal brain tumor cutting surface surrounding the brain tumor and determined based on the first position and/or the second position may be determined so that the cutting surface is minimized.

The brain tumor remover 740 may include various cutting devices and cutting modules to perform a cutting procedure on the brain tumor cutting surface.

The processor 750 may be implemented to control the operation of the image receiving and analyzing unit 700, the first positioner 710, the second positioner 720, the brain tumor cutting surface determiner 730, and the brain tumor remover 740.

Such a real-time brain tumor diagnosing method may be implemented in an antenna or in the form of programming commands executable through various computer components and may be recorded in a computer readable recording medium. The computer readable recording medium may include, individually or in combination, programming commands, data files, or data structures.

Programming commands recorded in the computer readable recording medium may be particularly designed or configured for the present invention or may be ones known and available to those skilled in the software art.

Examples of computer readable recording media include magnetic media, such as hard disks, floppy disks, and magnetic tapes, optical recording media, such as CD-ROMs and DVDs, magneto-optical media, such as floptical disks, and hardware devices particularly configured to retain and execute programming commands, such as ROMs, RAMs, and flash memories.

Examples of programming commands include machine-language code, such as those created by compilers, and high-class language code executable on computers by use of interpreters. The hardware devices may be configured to operate in one or more software modules and vice versa, to perform the processes as per the present invention.

Although embodiments have been described above, it will be appreciated by one of ordinary skill in the art that various changes and modifications may be made to the present invention without departing from the spirit and scope of the present invention defined in the claims.

What is claimed is:

1. A method for detecting a brain tumor in real-time, the method comprising:
producing a plurality of input signals and transferring the input signals to a target detection area where the brain tumor is estimated to be positioned, by a probe;
receiving a plurality of reflected signals based on the plurality of input signals, by the probe; and
detecting the plurality of reflected signals received, by the probe, wherein the plurality of input signals include a terahertz signal, an optical coherence tomography (OCT) signal, and a Raman signal, and wherein the plurality of reflected signals are used to produce information about a plurality of images to detect the position of the brain tumor, wherein the plurality of input signals further include a fluorescent signal, and wherein the terahertz signal is an electromagnetic wave in the form of a continuous wave or pulse wave having a frequency band ranging from 0.05 THz to 30 THz, the OCT signal is a signal with a wavelength ranging 600 nm to 1400 nm produced by a broadband wavelength light source for optical coherence tomography, the Raman signal is a signal with a wavelength ranging from 200 nm to 1400 nm produced by a broadband wavelength light source for Raman spectroscopy and imaging, and the fluorescent signal is a signal produced based on a contrast medium, wherein the plurality of reflected signals are total-reflected or transmitted by an indium tin oxide (ITO) glass, and wherein among the plurality of reflected signals, the terahertz signal is total-reflected by the ITO glass, and the OCT signal, the Raman signal, and the fluorescent signal are transmitted through the ITO glass, wherein the plurality of images include a first image, a second image, and a third image, and wherein the first image is a image produced based on the terahertz signal, the second image is an image produced based on the OCT signal, the Raman signal, and the fluorescent signal, and the third image is a fusion image of the first image and the second image.

2. The method of claim 1, further comprising:
producing a plurality of second input signals and transferring the second input signals to a brain tumor sample, by an in-vitro real-time brain tumor diagnosing apparatus;
receiving a plurality of second reflected signals based on the plurality of second input signals, by the in-vitro real-time brain tumor diagnosing apparatus; and
producing information about a plurality of images for the brain tumor sample based on the plurality of second reflected signals, by the in-vitro real-time brain tumor diagnosing apparatus, wherein the plurality of second input signals include a second terahertz signal, a second OCT signal, and a second Raman signal, and wherein each of the plurality of second input signals shares the same signal source as a respective one of the plurality of input signals.

* * * * *